US008697844B2

(12) United States Patent
Wiendahl et al.

(10) Patent No.: US 8,697,844 B2
(45) Date of Patent: Apr. 15, 2014

(54) METHOD OF PURIFYING PEGYLATED PROTEINS

(75) Inventors: Matthias Karl Dietrich Wiendahl, Hilleroed (DK); Lars Sejersgaard, Albertslund (DK); Are Bogsnes, Nivaa (DK)

(73) Assignee: Novo Nordisk A/S, Bagsvaerd (DK)

( * ) Notice: Subject to any disclaimer, the term of this patent is extended or adjusted under 35 U.S.C. 154(b) by 48 days.

(21) Appl. No.: 13/509,867

(22) PCT Filed: Nov. 24, 2010

(86) PCT No.: PCT/EP2010/068112
§ 371 (c)(1),
(2), (4) Date: Jun. 14, 2012

(87) PCT Pub. No.: WO2011/064247
PCT Pub. Date: Jun. 3, 2011

(65) Prior Publication Data
US 2012/0244137 A1   Sep. 27, 2012

Related U.S. Application Data

(60) Provisional application No. 61/264,486, filed on Nov. 25, 2009.

(30) Foreign Application Priority Data

Nov. 24, 2009 (EP) .................................. 09176881

(51) Int. Cl.
| | |
|---|---|
| A61K 35/14 | (2006.01) |
| C07K 14/745 | (2006.01) |
| A61K 38/43 | (2006.01) |
| A61K 38/57 | (2006.01) |
| A61K 38/54 | (2006.01) |
| C12N 9/96 | (2006.01) |
| C07K 1/00 | (2006.01) |
| C12P 21/06 | (2006.01) |
| C12P 21/04 | (2006.01) |
| C07K 1/06 | (2006.01) |
| C07K 14/00 | (2006.01) |

(52) U.S. Cl.
USPC ........ 530/384; 530/381; 530/387.1; 530/416; 530/412; 530/413; 514/13.7; 514/14.1; 514/14.3; 435/68.1; 435/69.6; 435/188; 424/94.3

(58) Field of Classification Search
USPC ....................... 424/94.3; 435/68.1, 69.6, 188; 514/13.7, 14.1, 14.3; 530/381, 384, 530/412, 413, 416, 417
See application file for complete search history.

(56) References Cited

U.S. PATENT DOCUMENTS

| | | | |
|---|---|---|---|
| 5,714,583 A | 2/1998 | Foster et al. | |
| 2002/0010319 A1 | 1/2002 | Ansaldi et al. | |
| 2006/0040856 A1* | 2/2006 | DeFrees et al. | 514/8 |
| 2007/0105755 A1* | 5/2007 | DeFrees et al. | 514/8 |
| 2008/0207879 A1 | 8/2008 | Artur et al. | |

FOREIGN PATENT DOCUMENTS

| | | |
|---|---|---|
| JP | 10-59867 B | 12/1989 |
| WO | WO 96/40731 | 12/1996 |
| WO | WO 2005/055950 | 6/2005 |
| WO | WO 2007/022512 | 2/2007 |
| WO | WO 2008/119815 | 10/2008 |

OTHER PUBLICATIONS

Isoelectric Point Calculator—ST3GAL3 (human), (http://www.phosphosite.org/isoelectricCalcAction.do;jsessionid=3E6357E00B537AF64C2AEDCD746E0DC0?id=23007202&residues), downloaded Nov. 8, 2012.*
Yun et al., "Reproducible Preparation and Effective Separation of Pegylated Recombinant Human Granulocyte Colony-Stimulating Factor With Novel "Peg-Pellet" Pegylation Mode and Ion-Exchange Chromatography", Journal of Biotechnology, 2005, Vol. 118, No. 1, pp. 67-74.
Hoffman and Monroe, Thrombosis and Haemostasis, 2001, Vol. 86, No. 6, pp. 958-965.
Schmidt, A.E. et al., "Structure-Function Relationships in Factorix and Factor IXa", Trends in Cardiovascular Medicine, 2003, Vol. 13, No. 1, pp. 39-45.
Harrison et al., "The Manufacturing Process For Recombinant", Seminars In Hematology, 1998, vol. 35, Part 2, pp. 4-10.
Yanding Zhao et al. Chinese Journal of Biologicals. "Seperation of Blood Coagulation Factor IX from Human Plasma by Self Made Chromatographic Media." 2008. vol. 21(10) pp. 906-908.

* cited by examiner

*Primary Examiner* — Jon P Weber
*Assistant Examiner* — Kailash C Srivastava
(74) *Attorney, Agent, or Firm* — Michael J. Brignati

(57) ABSTRACT

The invention relates to a method of purifying PEGylated proteins by removing impurities from samples containing PEGylated proteins, in particular, but not exclusively vitamin K-dependent blood coagulation factors such as Factor IX (FIX), to proteins purified by said method and to the use of said purified proteins in therapy, in particular but not exclusively, for the treatment of diseases alleviated by blood coagulation factors such as the prophylactic treatment of hemophilia.

11 Claims, 1 Drawing Sheet

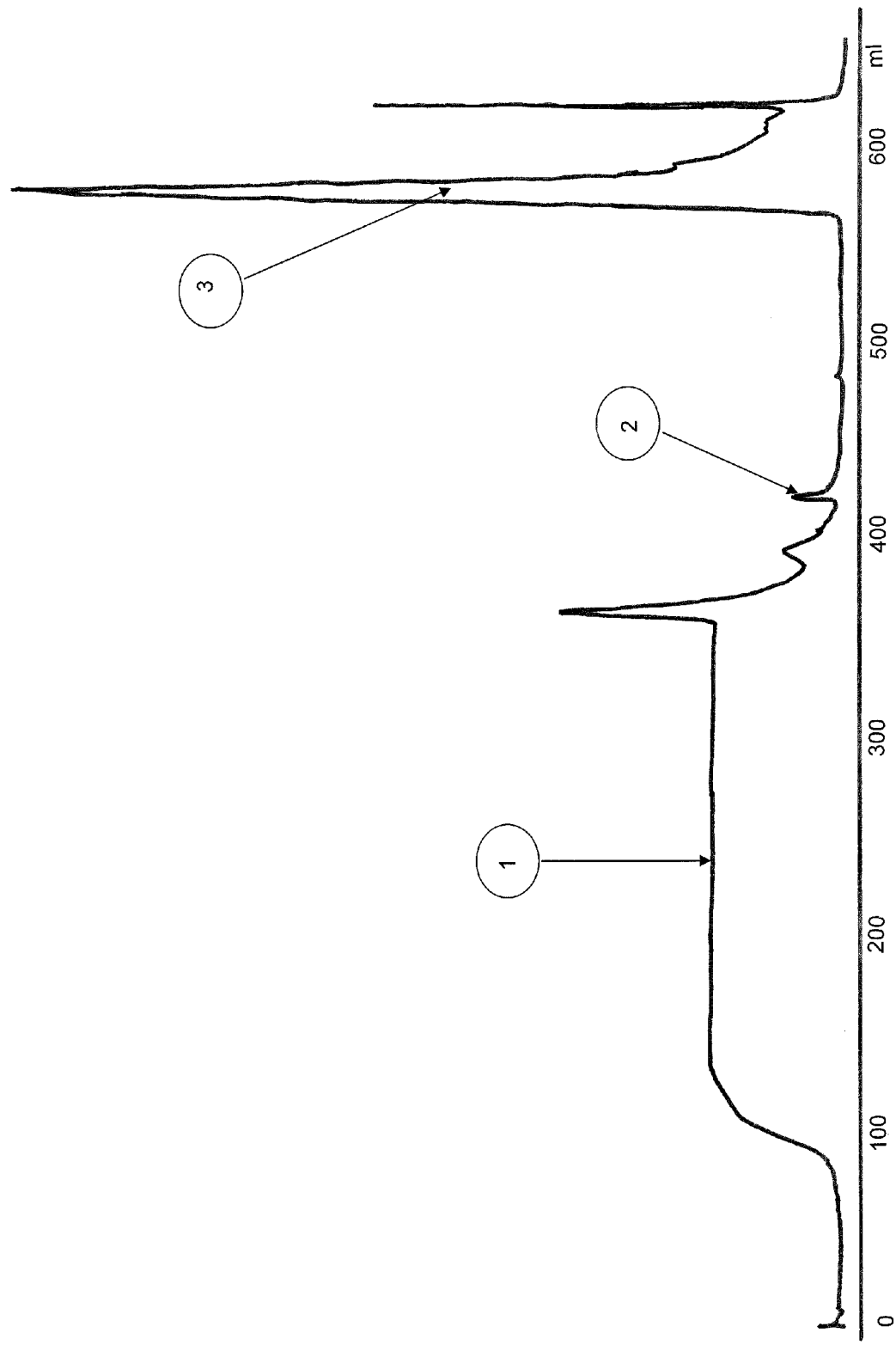

US 8,697,844 B2

METHOD OF PURIFYING PEGYLATED PROTEINS

CROSS-REFERENCE TO RELATED APPLICATIONS

This application is a 35 U.S.C. 371 national stage application of International Patent Application PCT/EP2010/068112 (published as WO 2011/064247 A1), filed Nov. 24, 2010, which claimed priority of European Patent Application 09176881.2, filed Nov. 24, 2009; this application further claims priority under 35 U.S.C. §119 of U.S. Provisional Application 61/264,486, filed Nov. 25, 2009.

FIELD OF THE INVENTION

The invention relates to a method of purifying PEGylated proteins by removing impurities from samples containing PEGylated proteins, in particular, but not exclusively vitamin K-dependent blood coagulation factors such as Factor IX (FIX), to proteins purified by said method and to the use of said purified proteins in therapy, in particular but not exclusively, for the treatment of diseases alleviated by blood coagulation factors such as the prophylactic treatment of hemophilia.

BACKGROUND OF THE INVENTION

Blood coagulation is a process consisting of a complex interaction of various blood components, or factors, which eventually gives rise to a fibrin clot. Generally, the blood components that participate in what has been referred to as the coagulation "cascade" are proenzymes or zymogens, enzymatically inactive proteins that are converted to proteolytic enzymes by the action of an activator, which is itself an activated clotting Factor. Coagulation factors that have undergone such a conversion are generally referred to as "active factors", and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilisation of factors present only in plasma. A series of protease-mediated activations ultimately generates Factor IXa, which, in conjunction with Factor VIIIa, cleaves Factor X into Xa. An identical proteolysis is effected by Factor VIIa and its co-Factor, tissue factor, in the "extrinsic pathway" of blood coagulation. Tissue factor is a membrane bound protein and does not normally circulate in plasma. Upon vessel disruption, however, it can complex with Factor VIIa to catalyse Factor X activation or Factor IX activation in the presence of $Ca^{2+}$ and phospholipid. The relative importance of the two coagulation pathways in haemostasis is still unclear.

Factor IXa (FIXa) is a trypsin-like serine protease that serves a key role in haemostasis by generating, as part of the Xase complex, most of the Factor Xa required to support proper thrombin formation during coagulation (reviewed in Hoffman M. and Monroe D. M., III (2001) A cell-based model of hemostasis. Thromb Haemost 85, 958-965). Congenital deficiency of Factor IXa activity is the cause of the X-linked bleeding disorder haemophilia B affecting approximately 1:100,000 males. These haemophilia patients are currently treated by replacement therapy with either recombinant or plasma-derived coagulation Factor IX.

Factor IX is a vitamin K-dependent coagulation factor with structural similarities to Factor VII, Factor X, and protein C. The circulating zymogen form, which has a plasma half-life of about 18-30 hours, consists of 415 amino acids divided into four distinct domains comprising an N-terminal γ-carboxyglutamic acid rich (Gla) domain, two EGF domains, and a C-terminal trypsin-like serine protease domain. Activation of Factor IX occurs by limited proteolysis at $Arg^{145}$-$Ala^{146}$ and $Arg^{180}$-$Val^{181}$ releasing a 35-aa fragment, the so-called activation peptide (Schmidt A. E. and Bajaj S. P. (2003) Structure-function relationships in Factor IX and Factor IXa. Trends Cardiovasc Med 13, 39-45). The activation peptide is heavily glycosylated containing two N-linked and up to four O-linked glycans.

Prolongation of circulating half-life of proteins can be achieved by modification of the native structure of the proteins. PEGylation is an established method for prolonging the circulating half-life of proteins. GlycoPEGylation of Factor IX (FIX) results in various PEGylated species such as mono-, di and tri-PEGylated species. Such an arrangement therefore provides the possibility for formation of various mono-PEGylated and di-PEGylated species. Mono-PEGylated forms have been identified to possess a desirable pharmacological profile and have therefore been chosen as the preferred drug candidate. It is thus desirable to isolate the mono-PEGylated forms from a mixture of PEGylated and non-PEGylated species.

In addition to separation of PEGylated species from each other and from nonPEGylated species, the purification process must provide sufficient reduction of reagents used in the reaction. It is required to develop a method that ensures the desired product quality and it will be advantageous to develop a single step of purification that can provide sufficient reduction of process related impurities (such as PEGylating reagents, enzymes, by products from reagents) as well as product related impurities (such as nonPEGylated species).

US 2008/207879 (Baxter Int) describes a purification process for rFIX which comprises loading the product onto an anion exchange column and washing the column with a salt concentration of more than 200 mM and eluting with an elution buffer containing divalent cations.

SUMMARY OF THE INVENTION

According to a first aspect of the invention, there is provided a method of purifying a PEGylated protein which comprises anion exchange chromatography with an elution buffer, characterized in that said chromatography comprises an impurity removal step prior to elution wherein said impurity removal step comprises washing said anion exchange column with an acidic buffer.

According to a second aspect of the invention, there is provided a purified PEGylated Factor IX blood coagulation factor obtainable by a method as herein defined.

BRIEF DESCRIPTION OF THE FIGURES

FIG. 1 shows a chromatogram obtained with the purification method of the invention.

DETAILED DESCRIPTION OF THE INVENTION

According to a first aspect of the invention, there is provided a method of purifying a PEGylated protein which comprises anion exchange chromatography with an elution buffer, characterized in that said chromatography comprises an impurity removal step prior to elution wherein said impurity removal step comprises washing said anion exchange column with an acidic buffer.

The purification method of the invention provides a number of advantages over previously described purification processes. It has been surprisingly found that the PEGylated protein (e.g. FIX) despite the acidic buffer—still is bound to the resin during washing. In so far the purification factor (the ratio of the concentration of PEGylated protein and impurities) is surprisingly high.

For example, the content of ST3 beta-galactoside alpha-2, 3-sialyltransferase 3 (ST3Gal3) in the resultant fractions was significantly reduced in the present invention. ST3Gal3 is a PEGylating enzyme used during the GlycoPEGylation process. The presence of such an enzyme in the resultant fractions is clearly undesirable because further PEGylation may occur following the purification process. Furthermore, residual enzyme is considered as an impurity and there is a desire to reduce the amount of residual enzyme to very low levels in pharmaceutical preparations of mono-PEGylated rFIXa.

The acidic wash step of the invention also provides the advantage of inactivating any pH sensitive viruses which may be present within the sample.

The invention also provides the further advantage of allowing purification in a single chromatographic step.

PEGylated proteins can be obtained by one of the known methods in the literature and known by the person skilled in the art. WO 2005/055950 and WO 2006/127896 describe methods for PEGylation of FIX where the PEG group is attached enzymatically to a glycosyl group. The PEGylation reaction mixture subjected to purification by the method of invention can be obtained by GlycoPEGylation or by other known PEGylation methods.

Although purification of PEGylated proteins constitutes a particular aspect of the invention, the method can also be equally applied to purification of proteins that are attached to polymers other than PEG, such as polysialic acid.

In one embodiment, the size of the attached PEG group varies from about 2 to about 40 KD.

In one embodiment, the impurity removed by the acidic wash step is ST3Gal3.

In one embodiment, the impurity removal step comprises washing with an acidic buffer at a pH of between 3.8 and 5.0 (i.e. at a pH of any one of 3.9, 4.0, 4.1, 4.2, 4.3, 4.4, 4.5, 4.6, 4.7, 4.8, 4.9 or 5.0), such as between 4.0 and 4.5 (i.e. at a pH of any one of 4.0, 4.1, 4.2, 4.3, 4.4 or 4.5), for example, between 4.0 and 4.4, in particular between 4.1 and 4.3, most particularly 4.1, 4.2, or 4.3. The advantage of performing the impurity removal step at a pH of below 4.5 is that the PEGylated protein will be bound tightly at such a pH due to the presence of $Ca^{2+}$ binding domains, therefore, the acidic wash can be used to reduce the concentration of other contaminants having a higher isoelectric point than the PEGylated protein.

It will be appreciated that the will comprise any suitable buffer capable of reducing the pH below about 4.5, however, suitably the buffer will not comprise a divalent cation. In one embodiment, the acidic buffer comprises sodium acetate and/or acetic acid. In a further embodiment, the acidic buffer comprises 50 mmol sodium acetate and 140 mmol acetic acid. It will be appreciated that lower concentrations of sodium acetate and acetic acid may be used, however, it is important that the ratio between these two components is kept constant and that the acidic wash step is sufficiently long to reduce pH to below 4.5.

It will be appreciated that the acidic wash step is performed prior to elution and following sample application to the anion exchange column. In one embodiment, an equilibration step is performed prior to the sample application step. The benefit of performing an equilibration step is that the unbound PEGylated protein is washed through the anion exchange column. In a further embodiment, the equilibration step comprises application of an equilibration buffer at a pH of between 5 and 7. The advantage of performing an equilibration step at a pH of between 5 and 7 is that the impurity cytidine-5'-monophospho-N-acetylneuraminic acid (CMP-NAN) surprisingly does not bind to the anion exchange column at such a pH and is therefore removed in the flowthrough.

In one embodiment, a second equilibration step is performed prior to the acidic wash step, although it will be appreciated that such a second equilibration step could be omitted (for example, the acidic wash step could directly follow the sample application step). The advantage of performing an equilibration step prior to the acidic wash step is the fact that ST3Gal3 is selectively eluted in a pH shift or pH gradient from equilibration conditions (e.g. at a pH of between 5 and 7) and the acidic wash conditions (e.g. at a pH of between 4 and 4.5). In a yet further embodiment, the equilibration step comprises application of an equilibration buffer at a pH of 6, such as a histidine containing buffer at a pH of 6.

In one embodiment, the equilibration buffer comprises sodium acetate and acetic acid. In a further embodiment, the equilibration buffer comprises 10 mM acetic acid and 90 mM sodium acetate.

It will be appreciated that the PEGylated sample may be applied to the anion exchange column following the equilibration step (i.e. after the equilibration step but prior to the acid wash step). The PEGylated sample may also be directly applied during the acidic wash step at pH 4-4.5, however, although this will result in significantly less binding of ST3Gal3, it is also possible that the ability of the anion exchange column to bind the PEGylated sample may be reduced.

In one embodiment, a third equilibration step is performed after the acidic wash step but prior to elution.

In one embodiment, the PEGylated protein is a vitamin K-dependent protein, such as a vitamin K-dependent blood coagulation factor. In a further embodiment, the vitamin K-dependent blood coagulation factor comprises a galactose containing blood coagulation factor. In a yet further embodiment, the vitamin K-dependent blood coagulation factor is selected from Factor II (FII), Factor VII (FVII), Factor IX (FIX), Factor X (FX), protein S and protein C. In a yet further embodiment, the vitamin K-dependent blood coagulation factor is Factor IX (FIX) or Factor VII (FVII). In a still yet further embodiment, the vitamin K-dependent blood coagulation factor is Factor IX (FIX).

In one embodiment of any of the aforementioned aspects of the invention, the Factor IX is selected from any of the non-limiting Factor IX derivatives disclosed in WO 03/031464, US 2005/0106658, WO 2004/099231, US 2004/0132640, US 2005/0100982, US 2004/0137557, US 2006/0030521, US 2004/0063911, US 2006/0040856, WO 2005/055950, WO 2006/127896 and WO 2008/119815. In a further embodiment, the Factor IX is PEG40k-FIX, as described in Example 1 of WO 2008/119815.

In one embodiment, where the Factor IX is PEG40k-FIX the lower limit of the pH-value for the acidic buffer of the impurity removal step is ca. pH 3.7-3.8 since PEG40k-FIX elutes at this pH.

It will be appreciated that anion exchange chromatography can be performed in accordance with procedures known to the skilled person. Examples of suitable anion exchange materials include: Q-resin, a Quaternary amine, and DEAE resin, DiEthylAminoEthane. Anion exchange resins are commercially available, e.g. Mono Q Source 15Q or 30Q (GE-health care), Poros 20HQ or 50HQ (Applied Biosystems), Toyopearl Q650S (Toso Haas) and others.

In one embodiment, the anion exchange material comprises HQ, such as Poros® HQ, for example, Poros® 50 HQ. Poros® HQ is available from Applied Biosystems and is based on a quaternized polyethyleneimine functional group yielding a high capacity.

According to a second aspect of the invention, there is provided a purified PEGylated protein obtainable by a method as herein defined.

In one embodiment, the PEGylated protein is a vitamin K-dependent protein, such as a vitamin K-dependent blood coagulation factor. In a further embodiment, the vitamin K-dependent blood coagulation factor comprises a galactose containing blood coagulation factor. In a yet further embodiment, the vitamin K-dependent blood coagulation factor is selected from Factor II (FII), Factor VII (FVII), Factor IX (FIX), Factor X (FX), protein S and protein C. In a yet further embodiment, the vitamin K-dependent blood coagulation factor is Factor IX (FIX) or Factor VII (FVII). In a still yet further embodiment, the vitamin K-dependent blood coagulation factor is Factor IX (FIX).

In one embodiment, the purified protein, such as a mono-PEGylated vitamin K-dependent protein is substantially free of ST3Gal3. By "substantially free" it is meant that the mono-PEGylated vitamin K-dependent protein contains less than 100 ng/mL of ST3Gal3.

In one embodiment, the purified protein, such as a mono-PEGylated vitamin K-dependent protein is substantially free of multiPEGylated species. By "substantially free" it is meant that the mono-PEGylated vitamin K-dependent protein contains less than 20% of multiPEGylated species, such as less than 15%, or less than 10% or less than 5%, less than 3%, less than 2% or less than 1%.

According to a further aspect of the invention there is provided a pharmaceutical composition comprising a purified PEGylated protein as herein defined, such as purified Factor IX.

The purified blood coagulation factors and pharmaceutical compositions comprising the blood coagulation factors may be used in the treatment of diseases alleviated by administration of blood coagulation factors (e.g. FIX), such as a bleeding disorder e.g. hemophilia, a blood disease, hemarthrosis, hematomas, mucocutaneous bleeding, inherited blood disease, familial bleeding disorder, familial blood disease or factor replacement therapy. In one embodiment, the disease alleviated by administration of a blood coagulation factor is hemophilia, such as hemophilia B or Christmas disease.

Thus according to a further aspect of the invention there is provided a method of treating hemophilia which comprises administering to a patient a therapeutically effective amount of a purified blood coagulation factor as defined hereinbefore.

There is also provided a purified blood coagulation factor as defined hereinbefore for use in the treatment of hemophilia.

There is also provided the use of a purified blood coagulation factor as defined hereinbefore in the manufacture of a medicament for the treatment of hemophilia.

There is also provided a pharmaceutical composition comprising a purified blood coagulation factor as defined hereinbefore for use in the treatment of hemophilia.

It is to be understood, that therapeutic and prophylactic (preventive) regimes represent separate aspects of the present invention. In particular, it should be understood that the present invention provides purified blood coagulation factors with increased plasma half-lives which make them desirable for the prophylactic treatment of hemophilia. Such prophylactic treatment of hemophilia constitutes a preferred embodiment of the invention.

The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In one embodiment of the invention the pharmaceutical formulation is an aqueous solution.

In one embodiment the pharmaceutical formulation is a freeze-dried formulation, whereto the physician or the patient adds solvents and/or diluents prior to use.

In one embodiment the pharmaceutical formulation is a dried formulation (e.g. freeze-dried or spray-dried) ready for use without any prior dissolution.

In one embodiment the invention relates to a pharmaceutical formulation comprising an aqueous solution of a purified blood coagulation factor of the present invention, and a buffer, wherein said purified blood coagulation factor is present in a concentration from 0.1-100 mg/ml, and wherein said formulation has a pH from about 2.0 to about 10.0.

In one embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In one embodiment of the invention the buffer is selected from the group consisting of sodium acetate, sodium carbonate, citrate, glycylglycine, (2-hydroxyethyl)-1-piperazineethanesulfonic acid (HEPES), 3-(N-morpholino)propanesulfonic acid (MOPS); 2-(N-morpholino)ethanesulfonic acid (MES); N-cyclohexyl-3-aminopropanesulfonic acid (CAPS); N-Cyclohexyl-2-aminoethanesulfonic acid (CHES); histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In one embodiment of the invention the formulation further comprises an active site inhibitor.

In one embodiment of the invention the formulation further comprises a pharmaceutically acceptable preservative. In one embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment of the invention the preservative is present in a concentration from 0.1 mg/ml to 20 mg/ml. In one embodiment of the invention the preservative is present in a concentration from 0.1 mg/ml to 5 mg/ml. In one embodiment of the invention the preservative is present in a concentration from 5 mg/ml to 10 mg/ml. In one embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In one embodiment of the invention the formulation further comprises an isotonic agent. In one embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. In one embodiment, the sugar or sugar alcohol concentration is between about 1 mg/ml and about 150 mg/ml. In one embodiment of the invention the isotonic agent is present in a concentration from 1 mg/ml to 50 mg/ml. In one embodiment of the invention the isotonic agent is present in a concentration from 1 mg/ml to 7 mg/ml. In one embodiment of the invention the isotonic agent is present in a concentration from 8 mg/ml to 24 mg/ml. In one embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a chelating agent. In one embodiment of the invention the chelating agent is selected from salts of ethylenediaminetetraacetic acid (EDTA), citric acid, and aspartic acid, and mixtures thereof. In one embodiment of the invention the chelating agent is present in a concentration from 0.1 mg/ml to 5 mg/ml. In one embodiment of the invention the chelating agent is present in a concentration from 0.1 mg/ml to 2 mg/ml. In one embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or mixtures thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used.

Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In one embodiment of the invention the amino acids or amino acid analogues are used in a concentration, which is sufficient to prevent or delay aggregation of the protein.

In one embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or mixtures thereof) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In one embodiment of the invention the formulation further comprises a stabilizer selected from the group of high molecular weight polymers or low molecular compounds. In one embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In one embodiment of the invention the formulation further comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)—derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), nonionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy,* 20*th* edition, 2000.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a purified blood coagulation factor of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of a peptide of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres and nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the peptide of the present invention in the form of a nasal or pulmonal spray. As a still further option, the pharmaceutical compositions containing the peptide of the present invention can also be adapted to transdermal administration, e.g. by needle-free injection or from a patch, optionally an iontophoretic patch, or transmucosal, e.g. buccal, administration.

The term "stabilized composition" refers to a composition with increased physical stability, increased chemical stability or increased physical and chemical stability.

The term "physical stability" of the protein composition as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to protein aggregation, when it shows visual turbidity in daylight. Alternatively, the turbidity of the composition can be evaluated by simple turbidity measurements well-known to the skilled person. Physical stability of the aqueous protein compositions can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment of the invention the pharmaceutical composition comprising the purified protein of the invention is stable for more than 6 weeks of usage and for more than 3 years of storage.

In another embodiment of the invention the pharmaceutical composition comprising the purified protein of the invention is stable for more than 4 weeks of usage and for more than 3 years of storage.

In a further embodiment of the invention the pharmaceutical composition comprising the purified protein of the invention is stable for more than 4 weeks of usage and for more than two years of storage.

In an even further embodiment of the invention the pharmaceutical composition comprising the purified protein of the invention is stable for more than 2 weeks of usage and for more than two years of storage.

In an even further embodiment of the invention the pharmaceutical composition comprising the purified protein of the invention is stable for more than 1 week of usage and for more than six months of storage.

The invention will now be described with reference to the following non-limiting examples.

EXAMPLE 1

Purification of PEGylated FIX (a) Load Solution
Buffer exchanged PEGylated FIX more than 95% pure. pH value in load is ca. 6. FIX-concentration is ca. 1 mg/mL. Load ca. 5 $g_{product}/L_{resin}$
(b) Column
Poros 50 HQ, 15.7 mL.
(c) Buffers
Equilibration buffer: 10 mM acetic acid, 90 mM sodium acetate, pH ~5.7
Acidic Wash: 5 CV acidic wash buffer: sodium acetate 65 mmol/kg, acetic acid: 185 mmol/kg pH ~4.3; 5 CV Elution: 5 CV linear gradient from 100% equilibration buffer to 100% Elution buffer (10 mM Histidine, 50 mM NaCl, 50 mM $CaCl_2$)
Regeneration: 3 CV 1 M NaCl
(d) Procedure

| Step | Buffer | CV | %-elution buffer |
|---|---|---|---|
| Equilibrate | Equilibration buffer | 5 | 0% |
| Application | | | |
| Wash | Equilibration buffer | 3 | 0% |
| Acidic wash (=wash 2) | Acidic wash buffer | 3 | 0% |
| Wash 3 | Equilibration buffer | 3 | 0% |
| Elution | Elution buffer | 5 | 0 . . . 100% |
| Regeneration | Regeneration buffer | 3 | 0% |

Flow rate: 24 CV/h = 6.28 ml/min
Temperature: 5° C.

The results of the chromatographic purification procedure are shown in FIG. 1 which depicts the chromatogram obtained with a UV280 nm-signal. The peak marked with a "1" depicts the flowthrough where e.g. CMP-NAN is removed. The peak marked with a "2" depicts the peak corresponding to ST3Gal3, i.e. it shows where ST3Gal3 is removed and the peak marked with "3" depicts the product peak.

The results of FIG. 1 clearly show that the product peak is visibly separated from the impurities such as ST3Gal3 and CMP-Nan, confirming the efficient purification provided by the method of the invention.

LIST OF EMBODIMENTS

Embodiment 1

A method of purifying a PEGylated protein which comprises anion exchange chromatography with an elution buffer, characterized in that said chromatography comprises an impurity removal step prior to elution wherein said impurity removal step comprises washing said anion exchange column with an acidic buffer.

Embodiment 2

The method of Embodiment 1, wherein the size of the attached PEG group varies from about 2 to about 40 KD.

Embodiment 3

The method of Embodiment 1 or Embodiment 2 wherein the impurity removed by the acidic wash step is ST3Gal3.

Embodiment 4

The method of any preceding Embodiments, wherein the impurity removal step comprises washing with an acidic buffer at a pH of between 3.8 and 5.0, 3.9 and 4.8 or 4.0 and 4.5.

Embodiment 5

The method of Embodiment 4 wherein the pH is 3.9, 4.0 or 4.1.

Embodiment 6

The method of Embodiment 4 wherein the pH is 4.2.

Embodiment 7

The method of Embodiment 4 wherein the pH is 4.3.

Embodiment 8

The method of Embodiment 4 wherein the pH is 4.4.

Embodiment 9

The method of Embodiment 4 wherein the pH is 4.5.

Embodiment 10

The method of Embodiment 4 wherein the pH is 4.6.

Embodiment 11

The method of Embodiment 4 wherein the pH is 4.7.

Embodiment 12

The method of Embodiment 4 wherein the pH is 4.8.

Embodiment 13

The method of Embodiment 4 wherein the pH is 4.9.

Embodiment 14

The method of Embodiment 4 wherein the pH is 5.0.

Embodiment 15

The method of Embodiment 4 wherein the pH is between 4.0 and 4.4.

Embodiment 16

The method of Embodiment 4 wherein the pH is between 4.1 and 4.3.

Embodiment 17

The method of any preceding Embodiments wherein the acidic buffer does not comprise a divalent cation.

Embodiment 18

The method of any preceding Embodiments wherein the acidic buffer comprises sodium acetate and/or acetic acid.

Embodiment 19

The method of any preceding Embodiments wherein the acidic buffer comprises 50 mmol sodium acetate and 140 mmol acetic acid.

Embodiment 20

The method of any preceding Embodiments wherein an equilibration step is performed prior to the sample application step.

Embodiment 21

The method of Embodiment 20 wherein the equilibration step comprises application of an equilibration buffer at a pH of between 5 and 7.

Embodiment 22

The method of Embodiment 20 or Embodiment 21 wherein a second equilibration step is performed prior to the acidic wash step.

Embodiment 23

The method of any of Embodiments 20 to 22 wherein the equilibration step comprises application of an equilibration buffer at a pH of 6.

Embodiment 24

The method of Embodiment 23 wherein the equilibration buffer is a histidine containing buffer at a pH of 6.

Embodiment 25

The method of any of Embodiments 21 to 24 wherein the equilibration buffer comprises sodium acetate and acetic acid.

Embodiment 26

The method of any of Embodiments 21 to 25 wherein the equilibration buffer comprises 10 mM acetic acid and 90 mM sodium acetate.

Embodiment 27

The method of any of Embodiments 22 to 26 wherein a third equilibration step is performed after the acidic wash step but prior to elution.

Embodiment 28

The method of any preceding Embodiments wherein the PEGylated protein is a vitamin K-dependent protein.

Embodiment 29

The method of Embodiment 28 wherein the PEGylated protein is a vitamin K-dependent blood coagulation factor.

Embodiment 30

The method of Embodiment 28 or Embodiment 29 wherein the PEGylated protein is a galactose containing blood coagulation factor.

Embodiment 31

The method of any of Embodiments 28 to 30 wherein the PEGylated protein is a vitamin K-dependent blood coagulation factor selected from Factor II (FII), Factor VII (FVII), Factor IX (FIX), Factor X (FX), protein S and protein C.

Embodiment 32

The method of any of Embodiments 28 to 31 wherein the PEGylated protein is Factor IX (FIX) or Factor VII (FVII).

Embodiment 33

The method of any of Embodiments 28 to 32 wherein the PEGylated protein is Factor IX (FIX).

Embodiment 34

The method of any of Embodiments 28 to 30 wherein the PEGylated protein is PEG40k-FIX.

Embodiment 35

The method of any preceding Embodiments wherein anion exchange chromatography comprises: Q-resin, a Quaternary amine, and DEAE resin, DiEthylAminoEthane.

Embodiment 36

The method of Embodiment 35 wherein the anion exchange resin is Mono Q Source 15Q or 30Q (GE-health care), Poros 20HQ or 50HQ (Applied Biosystems) or Toyopearl Q650S (Toso Haas).

Embodiment 37

The method of Embodiment 36 wherein the anion exchange material comprises HQ.

Embodiment 38

The method of Embodiment 37 wherein the anion exchange material comprises Poros® HQ.

Embodiment 39

The method of Embodiment 38 wherein the anion exchange material comprises Poros® 50 HQ.

Embodiment 40

A purified PEGylated protein obtainable by a method as defined in any preceding Embodiments.

Embodiment 41

Purified PEGylated FIX protein obtainable by a method as defined in any of Embodiments 1 to 39.

Embodiment 42

A purified PEGylated protein as defined in Embodiment 40 or Embodiment 41 which is substantially free of ST3Gal3.

Embodiment 43

A purified PEGylated protein as defined in any of Embodiments 40 to 42 which contains less than 100 ng/mL of ST3Gal3.

Embodiment 44

A purified PEGylated protein as defined in any of Embodiments 40 to 43 which is substantially free of multiPEGylated species.

Embodiment 45

A purified PEGylated protein as defined in any of Embodiments 40 to 44 which contains less than 20% of multiPEGylated species.

Embodiment 46

A purified PEGylated protein as defined in any of Embodiments 40 to 45 which contains less than 15% of multiPEGylated species.

Embodiment 47

A purified PEGylated protein as defined in any of Embodiments 40 to 46 which contains less than 10% of multiPEGylated species.

Embodiment 48

A purified PEGylated protein as defined in any of Embodiments 40 to 47 which contains less than 5% of multiPEGylated species.

Embodiment 49

A purified PEGylated protein as defined in any of Embodiments 40 to 48 which contains less than 3% of multiPEGylated species.

Embodiment 50

A purified PEGylated protein as defined in any of Embodiments 40 to 49 which contains less than 2% of multiPEGylated species.

Embodiment 51

A purified PEGylated protein as defined in any of Embodiments 40 to 50 which contains less than 1% of multiPEGylated species.

Embodiment 52

A pharmaceutical composition comprising a purified PEGylated protein as herein defined as defined in any of Embodiments 40 to 51.

Embodiment 53

A pharmaceutical composition comprising a purified PEGylated Factor IX protein.

Embodiment 54

A purified PEGylated protein as defined in any of Embodiments 41 to 51 or a pharmaceutical composition as defined in Embodiment 53 for use in the treatment of diseases alleviated by administration of blood coagulation factors (e.g. FIX), such as a bleeding disorder e.g. hemophilia, a blood disease, hemarthrosis, hematomas, mucocutaneous bleeding, inherited blood disease, familial bleeding disorder, familial blood disease or factor replacement therapy.

Embodiment 55

A purified PEGylated protein as defined in any of Embodiments 41 to 51 or a pharmaceutical composition as defined in Embodiment 53 for use in the treatment of hemophilia.

Embodiment 56

A purified PEGylated protein as defined in any of Embodiments 41 to 51 or a pharmaceutical composition as defined in Embodiment 53 for use in the treatment of hemophilia B or Christmas disease.

Embodiment 57

A method of treating hemophilia which comprises administering to a patient a therapeutically effective amount of a purified blood coagulation factor as defined in Embodiments 41 to 51.

Embodiment 58

Use of a purified blood coagulation factor as defined in Embodiments 41 to 51 in the manufacture of a medicament for the treatment of hemophilia.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A method for purifying a PEGylated protein which comprises performing anion exchange chromatography with an elution buffer, characterized in that said chromatography comprises an impurity removal step prior to elution wherein said impurity removal step comprises washing said anion exchange column with an acidic buffer at a pH of between 3.9 and 4.5, wherein the PEGylated protein is selected from the group consisting of Factor II (FII), Factor VII (FVII), Factor IX (FIX), Factor X (FX), protein S and protein C.

2. The method of claim 1, wherein said impurity is ST3 beta-galactoside alpha-2,3-sialyltransferase 3 (ST3Gal3).

3. The method of claim 1, wherein the impurity removal step comprises washing with an acidic buffer at a pH of selected from the group consisting of between 4.0 and 4.5 and between 4.0 and 4.4.

4. The method of claim 1, wherein the acidic buffer comprises sodium acetate or acetic acid, wherein the concentration of sodium acetate is about 50 mM, and wherein the concentration of acetic acid is about 140 mM.

5. The method of claim 1, wherein an equilibration step is performed prior to the acidic wash step.

6. The method of claim 5, wherein the equilibration step comprises application of an equilibration buffer at a pH of between 5 and 7.

7. The method of claim 5, wherein the equilibration buffer comprises sodium acetate and acetic acid, wherein the concentration of acetic acid is about 10 mM, and wherein the concentration of sodium acetate is about 90 mM sodium.

8. The method of claim 1, wherein the PEGylated protein is selected from the group consisting of Factor IX (FIX) and Factor VII (FVII).

9. The method of claim 1, wherein the anion exchange material comprises HQ.

10. The method of claim 9, wherein the HQ anion exchange material comprises Poros® HQ.

11. The method of claim 9, wherein the HQ anion exchange material comprises Poros® 50 HQ.

* * * * *